United States Patent [19]

George et al.

[11] Patent Number: 5,795,771
[45] Date of Patent: Aug. 18, 1998

[54] **CULTURE MEDIUM FOR *SACCHAROMYCES CEREVISIAE***

[75] Inventors: Hugh George, Schwenksville; Wayne K. Herber, Center Valley, both of Pa.

[73] Assignee: Merck & Co., Inc., Rahway, N.J.

[21] Appl. No.: 578,719

[22] PCT Filed: Jun. 28, 1994

[86] PCT No.: PCT/US94/07264

§ 371 Date: Apr. 8, 1996

§ 102(e) Date: Apr. 8, 1996

[87] PCT Pub. No.: WO95/01422

PCT Pub. Date: Jan. 12, 1995

Related U.S. Application Data

[63] Continuation of Ser. No. 86,216, Jul. 1, 1993, abandoned.

[51] Int. Cl.$^6$ .................... A01N 63/00; C12N 1/14; C12N 1/16; C12N 1/18
[52] U.S. Cl. .................... 435/255.21; 424/93.51; 435/255.2
[58] Field of Search .................... 424/93.51; 435/255.2, 435/255.21

[56] References Cited

U.S. PATENT DOCUMENTS 4,855,238  8/1989  Gray et al. .................... 435/243

OTHER PUBLICATIONS

Carty, et al., "Fermentation of Recombinant Yeast Producing Hepatatis B Surface Antigen", J. Ind. Microbio., vol. 2, pp. 117–121 (1987).

Zabriski, et al., "Factors Influencing Productivity of Fermentations Employing Recombinant Microorganisms", Enzyme Microb. Technol., vol. 8, pp. 706–171 (1986).

Jung, et al., "Supplement of Nutrients for Effective Cultivation of Hepatitis B Surface Antigen–Producing Recombinant Yeast", Biotechnol. Letters, vol. 13, pp. 857–862 (1991).

Oshima, et al., "Regulatory Circuits for Gene Expression: The Metabolism of Galactose and Phosphate in the Molecular Biology", vol. 1, pp. 159–180 (1981).

O'Connor, et al., "Design and Evaluation of Control Strategies for High Cell Density Fermentations", Biotechnol. and Bioengin., vol. 39, pp. 293–304 (1992).

Kitano, et al., "Recombinant Hepatitis B Virus Surface Antigen P31 Accumulates as Particles in *Saccharomyces cerevisiae*", Biotechnol., vol. 5, pp. 281–283 (1987).

Li, et a., "Hyper–resistance to Nitrogen Mustard in *Saccharomyces cerevisiae* is Caused by Defective Choline Transport", Curr. Genet., vol. 19, pp. 423–427 (1991).

Bailis, et al., "Cis and Trans Regulatory Elements Required for Regulation of the CHO1 Gene of *Saccharomyces cerevisiae*", Nucleic Acids Red., vol. 20, No. 6, pp. 1411–1418 (1992).

ATCC Catalogue of Funji Yeasts, 17th Edition, pp. 412–413 (1987).

*Primary Examiner*—David M. Naff
*Assistant Examiner*—Deborah K. Ware
*Attorney, Agent, or Firm*—Michael D. Yablonsky; Jack L. Tribble

[57] ABSTRACT

A synthetic culture medium for the growth of recombinant yeast and the production of recombinant proteins. The medium is useful for the growth of *Saccharomyces cerevisiae* which comprises per liter about 10 g ammonium sulfate, about 10 g potassium phosphate, about 0.5 g calcium chloride, about 0.5 g sodium chloride, about 3 g magnesium sulfate, about 0.25 g L-tyrosine, about 0.1 g choline, between about 1 and about 100 g carbon source, between about 50–150 mL amino acid cocktail, about 30 mL vitamin solution, about 20 mL trace element solution and about 0.3 mL UCON LB-625 antifoaming agent. Further, the vitamin solution contains biotin, pantothenate, myo-inositol, pyridoxine and thiamine.

8 Claims, No Drawings

CULTURE MEDIUM FOR *SACCHAROMYCES CEREVISIAE*

CROSS-RELATED TO OTHER APPLICATIONS

This application is a 371 of PCT/US94/07264, filed Jun. 28, 1994 and a continuation of U.S. Ser. No. 08/086,216, filed Jul. 1, 1993, now abandoned.

BACKGROUND OF THE INVENTION

Production of compounds of pharmaceutical significance by cultivation of recombinant yeasts is an expanding field of science and commerce. Purified recombinant hepatitis B surface antigen (HBSAg) is used as a vaccine for hepatitis B viral disease and is a well-known example of a pharmaceutically-significant recombinant protein.

Recombinant HBSAg is produced by fermentation of yeast in either complex or chemically-defined (synthetic) culture media. Generally, complex media, which contain crude sources of carbon and nitrogen such as yeast extract and peptones, support higher yields of cells and crude HBSAg than are achieved in synthetic media. However, fermentations performed in complex media are also more variable than fermentations which employ synthetic media. Inconsistencies in the fermentation adversely affect downstream purification steps and may also increase the cost of purified HBSAg.

Regulated expression systems are commonly used for the production of recombinant proteins. One type of regulated system provides tight nutritional control of the production of heterologous protein. This type of system maximizes biomass production and product stability while minimizing the adverse effects of heterologous protein expression on the host cell (Zabriskie et al., *Enzyme Microbial Technol.* 8:706–717 (1986)). Various components of the tightly-regulated galactose utilization pathway in yeast have been exploited successfully for controlled expression of a number of recombinant proteins, including portions of the hepatitis B envelope proteins (Carty et al., *Biotech. Lett*11:301–306, 1989)). Synthesis of proteins under the control of the GAL1 or GAL10 promoters occurs only in the presence of galactose and the absence of glucose (Oshima, 1981, Regulatory Circuits for Gene Expression: The Mechanism for Galactose and Phosphate. In: *The Molecular Biology of the Yeast Saccharomyces*, Vol. 1, pp. 159–180, Strathen, Jones, and Broach, (Eds.), Cold Spring Harbor Laboratory, Cold Spring Harbor, N.Y.). Most regulated expression systems function in both complex and synthetic culture media.

It would be desirable to identify the component(s) of complex media that affect fermentation yields. It would also be desirable to determine a formulation of synthetic culture medium that supported the production of recombinant protein more nearly equivalent to that achieved in complex media. Advantages of such discoveries would include the establishment of a more reproducible fermentation process and a more predictable purification process.

YEHD medium is one of many complex media that is used for the production of recombinant HBSAg. YEHD contains (per liter of distilled water) 20 g yeast extract powder, 10 g soy peptone and 16 g glucose. The amount of crude HBSAg produced when recombinant yeast are cultivated in YEHD varies from fermentation to fermentation.

Preliminary studies identified yeast extract powder as the component of YEHD responsible for a major part of the variability in fermentation yields. Chemical analyses of different manufacturing lots of yeast extract powder showed that the concentrations of at least six components of yeast extract powder varied significantly between lots. Further analyses of additional lots of yeast extract powder identified choline as a component of yeast extract powder that was strongly correlated with the productivity of the fermentation.

These data were used in the development of a synthetic culture medium that supports the growth of yeast cells and the production of recombinant proteins. The synthetic culture medium of the present invention differs from other synthetic media used to cultivate recombinant yeast in that it contains choline. The culture medium of the present invention may be used to prepare stock cultures of recombinant strains of *Saccharomvces cerevisiae*, including but not limited to strains of *S. cerevisiae* that produce hepatitis B surface antigen. The culture medium of the present invention may also be used to produce crude recombinant proteins, including but not limited to crude HBSAg. One of the advantages of this medium is the elimination of complex sources of nitrogen and carbon from the fermentation process. The elimination of the complex components minimizes the fluctuations due to fermentation variability and standardizes the amount and quality of the crude recombinant protein delivered to the purification stream.

SUMMARY OF THE INVENTION

A chemically-defined culture medium useful for the cultivation of recombinant yeasts and a process for the production of recombinant proteins is provided. The medium is particularly useful for the cultivation of strains of *Saccharomvces cerevisiae* which produce hepatitis B surface antigen. The culture medium does not contain complex sources of carbon and nitrogen but does contain choline.

DETAILED DESCRIPTION OF THE INVENTION

The present invention is related to a chemically-defined culture medium and a general fermentation process for the production of recombinant proteins by yeast cells. The process of the present invention is demonstrated with the production of a recombinant hepatitis B surface antigen (HBSAg) by strains of *Saccharomyces cerevisiae* transformed with a plasmid comprising the gene for HBSAg. As will be appreciated by one of ordinary skill in the art, the process of the present invention has a more general application to cultivation of other strains of *S. cerevisiae* and the production of other recombinant products and is not limited to recombinant HBSAg.

The present invention is directed to a fermentation process which employs a synthetic culture medium. Synthetic culture medium as used herein is defined as a mixture which supports the growth of yeast cells, which mixture contains only chemically-defined ingredients and which mixture further is devoid of complex nutrient components such as peptone, soy peptone, yeast extract powder, yeast dialysates, corn starch, molasses or casein. The synthetic medium disclosed herein is designed to minimize run-to-run variations in product yields that are associated with fermentations performed in complex culture media.

One preferred formulation of the medium of this invention is a modified formulation of a medium described by O'Connor et al., (1992, *Biotechnol. Bioengineer.* 39: 293–304), and contains:

| Base medium | |
|---|---|
| Ingredient | g/L |
| $(NH_4)_2SO_4$ | 10 |
| $KH_2PO_4$ | 10 |
| $CaCl_2.2H_2O$ | 0.5 |
| NaCl | 0.5 |
| $MgSO_4.7H_2O$ | 3 |
| L-tyrosine | 0.25 |
| Choline Chloride | 0.1 |
| Carbon source | .between 1 and 100 g/L |
| Amino acid cocktail | 50–150 mL/L |
| Vitamin solution | 30 mL/L |
| Trace element solution | 20 mL/L |
| UCON LB-625 antifoam | 0.3 mL/L |
| Succinic acid/NaOH | 10 g (optional) |
| Adenine | 150–400 mg/L (optional) |
| Uracil | 400 mg/L (optional) |

Amino acid cocktail contains (g/L in the stock solution): L-arginine, 2.0; L-histidine, 1.0; L-isoleucine, 6.0; L-lysine, 4.0; L- methionine, 1.0; L-phenylalanine, 6.0; L-tryptophan, 4.0.

Vitamin solution contains (mg/L in the stock solution): biotin, 10; Ca pantothenate, 120; myo-inositol, 600; pyridoxine.HCl, 120; thiamine.HCl, 120.

Trace element solution contains (mg/L in the stock solution): $FeSO_4.7H_2O$, 278; $ZnSO_4.7H_2O$, 288; $CuSO_4.5H_2O$, 80; $Na_2MoO_4.2H_2O$, 242; $CoCl_2.6H_2O$, 238; $MnCl_2.4H_2O$, 198.

Carbon sources are selected from the group consisting of glucose, sucrose, fucose, fructose, glycerol, ethanol, formic acid, lactic acid and combinations thereof.

Adenine and uracil are added if the host strains are auxotrophic for adenine and uracil.

Succinic acid and NaOH are added to shake flask formulations and are used to control the pH at about pH 5.0.

This specific formulation has been named HJW medium. However, it should be understood that the very precise amounts of ingredients provided above may be optimized, or modified so long as no complex media components are introduced. One advantage of the medium is the absence of complex sources of carbon and nitrogen, which improves the consistency of the medium and the reproducibility of fermentation processes employing the medium. Another advantage of the medium is the presence of choline in the medium. Choline increases the growth of certain strains of S. cerevisiae and also increases the production of recombinant proteins (such as HBSAg) by recombinant yeasts.

The foregoing description provides a basis for modifying the specific medium formulation of this invention, while maintaining the key feature of being free of complex sources of carbon, nitrogen and vitamins.

HJW agar is HJW medium supplemented with approximately 20 g/L agar.

HJW medium may be used to prepare stock cultures of recombinant yeasts. One method of preparing a stock culture comprises the steps of (a) growing a culture of S. cerevisiae on HJW agar; (b) selecting a single colony from the agar for expansion of the culture in HJW medium, and optionally preparing a frozen stock of the culture; and(c) growing a culture derived from the single colony in HJW medium, at between about 23° C. and about 30° C., for about 24–100 hours, with the length of cultivation varying according to the cultured species. Glycerol or other cryopreservatives known in the art can be added to cultures grown in HJW medium to maintain viability of frozen stocks. Preferably, glycerol is added to a final concentration between about 15% and about 25%, and preferably 17%.

HJW medium may also be used in a fermentation process for the production of a recombinant protein. One such fermentation process comprises the steps of (a) inoculating a flask containing HJW medium with a culture; (b) growing the culture at between about 23° C. and about 30° C., for about 15–80 hours, with the length of cultivation varying according to the cultivated strain; (c) transferring all or a portion of the flask culture to a second container of medium and continuing the cultivation at between about 23° C. and about 30° C. for about 20–80 hours, with the length of cultivation varying according to the cultured species; (d) optionally, altering the conditions of incubation (for example, by adding a compound such as galactose or by changing the temperature); and (e) recovering the crude recombinant product.

The following Examples are provided to illustrate the present invention without, however, limiting the same thereto.

EXAMPLE 1
Chemical Analyses of Samples of Yeast Extract Powders

The chemical compositions of two lots of yeast extract powder were determined. Lot #1 is a lot which supported the production of relatively high levels of crude HBSAg. Lot #2 is a lot that supported the production of several-fold lower yields of HBSAg. As shown in Table 1, the concentrations of at least six components of the yeast extract powders varied significantly. The effects of these components were examined further. The effects of choline on cell growth and product yield are reported below.

TABLE 1

| Chemical Composition of Yeast Extract Powders | | |
|---|---|---|
| Assay | Lot #1 | Lot #2 |
| free ammonium | 0.27% | 0.3% |
| ash | 13.30% | 10.60% |
| biotin | 2.52 ppm | 3.24 ppm |
| riboflavin | 65.3 ppm | 88.1 ppm |
| pyridoxine | 58.9 ppm | 45.9 ppm |
| calcium | 928 ppm | 309 ppm |
| choline chloride | 3604 ppm | 1257 ppm |
| cobalt | <1 ppm | <1 ppm |
| chromium | 2.09 ppm | 2.73 ppm |
| copper | 2.50 ppm | 2.47 ppm |
| iron | 42.9 ppm | 67.1 ppm |
| fat (acid hydrolysis) | 0.31% | 0.30% |
| inositol | 975 ppm | 559 ppm |
| potassium | 67100 ppm | 52250 ppm |
| magnesium | 694 ppm | 608 ppm |
| manganese | <1 ppm | 1.71 ppm |
| molybdenum | <12 ppm | <12 ppm |
| moisture | 3.50% | 3.14% |
| sodium | 5460 ppm | 6935 ppm |
| nickel | <8 ppm | <8 ppm |
| niacin | 796 ppm | 716 ppm |
| pantothenic acid | 180 ppm | 160 ppm |
| phosphorus | 1.63% | 1.14% |
| protein | 64.70% | 66.30% |
| zinc | 66.9 ppm | 95.7 ppm |

EXAMPLE 2
Expression Systems

Two recombinant strains of S. cerevisiae were used in this study. Strains 1375 and 181-1 were obtained from H. Markus and L. Schultz, Merck Research Laboratories, West Point, Pa. The expression plasmid has been described elsewhere (Kniskern, P. J., A. Hagopian, D. L. Montgomery, C. E. Carty, P. Burke, C. A. Schulman, K. J. Hofmann, F. J. Bailey, N. R. Dunn, L. D. Schultz, W. M. Humi, W. J. Miller, R. W. Ellis, and R. Z. Maigetter. 1991. Constitutive and regulated expression of the hepatitis B virus (HBV) PreS2+S protein in recombinant yeast. In, R. T. Hatch, C. Goochee, A. Moreira, and Y. Alroy (Eds.). Expression systems and processes for rDNA products. American Chemical Society, Columbus, Ohio) and incorporates the following features: the high-copy number shuttle vector pC1/1, the LEU2 gene for selection in leucine-free medium and an expression cassette containing open reading frame coding for HBSAg under the control of the yeast promoter pGAL10. Host strain 1372, the parent strain of Strain 1375, contains a mnn9 mutation to minimize glycosylation. The host strain for recombinant strain 181-1 was also derived from strain 1372 and contains a prb1 mutation to minimize proteolysis of the recombinant protein.

EXAMPLE 3
Optimization of Synthetic Medium

Frozen stock cultures of strain 1375 and 181-1 were used to inoculate 50 mL of 5× Leu⁻ medium (M. Bayne et al. 1988. Expression, purification and characterization of recombinant human insulin-like growth factor in yeast. *Gene* 66: 235) in 250 mL Erlenmeyer flasks. The 50 mL cultures were designated as seed cultures. The seed cultures were incubated at 28° C. and 250 rpm for between 26 and 31 hours.

Five mL aliquots of the seed cultures were used to inoculate production flasks. Each production flask contained basal synthetic medium supplemented with a different amount of choline chloride.

Production flask cultures were incubated at 23° C., 250 rpm for approximately 72 hours. Cell mass was determined by dry cell weight (DCW) and optical density ($OD_{600}$) while production of crude HBSAg was determined by AUSRLA®.

Basal synthetic medium is similar to the medium described by O'Connor et al. (*Biotech. Bioengin.* 39:293–304 (1992)) and contains:

| Ingredient | Base medium g/L |
|---|---|
| $(NH_4)_2SO_4$ | 10 |
| $KH_2PO_4$ | 10 |
| $CaCl_2.2H_2O$ | 0.5 |
| NaCl | 0.5 |
| $MgSO_4.7H_2O$ | 3 |
| L-tyrosine | 0.25 |
| Carbon source | between 1 and 100 g/L |
| Amino acid cocktail | 50–150 mL/L |
| Vitamin solution | 30 mL/L |
| Trace element solution | 20 mL/L |
| UCON LB-625 antifoam | 0.3 mL/L |
| Succinic acid/NaOH | 10 (optional) |
| Adenine | 150–400 mg/L |
| Uracil | 400 mg/L |

Amino acid cocktail contains (g/L in the stock solution): L-arginine, 2.0; L-histidine, 1.0; L-isoleucine, 6.0; L-lysine, 4.0; L-methionine, 1.0; L-phenylalanine, 6.0; L-tryptophan, 4.0.

Vitamin solution contains (mg/L in the stock solution): biotin, 10; Ca pantothenate, 120; myo-inositol, 600; pyridoxine.HCl, 120; thiamine-HCl, 120.

Trace element solution contains (mg/L in the stock solution): $FeSO_4.7H_2O$, 278; $ZnSO_4.7H_2O$, 288; $CuSO_4.5H_2O$, 80; $Na_2MoO_4.2H_2O$, 242; $CoCl_2.6H_2O$, 238; $MnCl_2.4H_2O$, 198.

Carbon sources are selected from the group consisting of glucose, sucrose, fucose, fructose, glycerol, ethanol, formic acid, lactic acid and combinations thereof.

Adenine and uracil are added if the host strains are auxotrophic for adenine and uracil.

Succinic Acid and NaOH are added to shake flask formulations so as to maintain the pH at approximately 5.0.

Choline chloride was added to final concentrations of 0, 50, 100 and 300 mg/L. As shown in Table 2, optimal cell growth and production of crude HBSAg for strain 1375 occurred when the concentration of choline was approximately 100 mg/L.

TABLE 2

Effect of Choline on Growth and HBSAg Production

| Strain | Choline Chloride (mg/L) | DCW (g/L) | Crude HBSAg |
|---|---|---|---|
| 1375 | 0 | 5 | 1 |
| | 50 | 16 | 2.1X |
| | 100 | 16 | 2.3X |
| | 300 | 10 | 1.8X |

The optimum formulation of the basal synthetic contains choline chloride (100 mg/L) and medium.

EXAMPLE 4
Effect of Carbon Source on Shake Flask Fermentations

Frozen stock cultures of strain 1375 were used to inoculate 50 mL of 5× Leu⁻ medium in 250 mL Erlenmeyer flasks. The 50 ML cultures were designated as seed cultures. The seed cultures were incubated at 28° C. and 250 rpm for between 26 and 31 hours.

Five mL aliquots of the seed cultures were used to inoculate production flasks. Each production flask contained HJW medium. Several carbon sources were tested. Production flask cultures were incubated at 23° C. and 250 rpm for approximately 72 hours. Cell mass was determined by dry cell weight (DCW) and optical density ($OD_{600}$) while production of crude HBSAg was determined by a commercially-available radioimmunoassay (AUSRIA®). As shown in Table 3, galactose supported maximum cell growth. All cultures produced HBSAg.

TABLE 3

Effect of Carbon Source on Growth of Strain 1375

| Carbon Source | $OD_{600}$ |
|---|---|
| Glucose | 10.1 |
| Sucrose | 10.1 |
| Fructose | 11.8 |
| Galactose | 16.9 |

EXAMPLE 5
Production of HBSAg in Fermentors

A frozen stock culture of strain 1375 was used to inoculate 500 mL of 5× leu⁻ medium in a 2-L flask. The culture was incubated at 28 C, 250 rpm for 23 hr. Five hundred mL was used to inoculate 9.5-L HJW medium in a 16-L fermentor (New Brunswick Scientific, Piscataway, N.J.). Galactose (8% w/v) was used as a source of carbon. The culture was incubated under the following conditions: 23° C., 400 rpm (with automatic increases in agitation to maintain greater dissolved oxygen levels greater than 40% of saturation), and airflow 5 lpm. The pH of the medium was controlled at approximately pH 5.0 by the automatic addition of NaOH and HCl. The final DCW was 14 g/L. The amount of crude HBSAg produced was equivalent to that achieved in shake flask fermentations.

EXAMPLE 6
Preparation of stock cultures

A frozen culture of *S. cerevisiae* strain 1375 is resuspended in HJW medium and incubated for about 48 hours at about 23° C. Glycerol is added to a final concentration of approximately 17%, and the culture is aliquoted and frozen at about −70° C. These cultures are designated as master stock cultures. The master stock cultures are subsequently expanded in HJW broth to make additional vials, which are designated as working stock cultures.

What is claimed is:

1. A medium for the growth of *Saccharomyces cerevisiae* which comprises per liter:

| | |
|---|---|
| $(NH_4)_2SO_4$ | about 10 g |
| $KH_2PO_4$ | about 10 g |
| $CaCl_2.2H_2O$ | about 0.5 g |
| NaCl | about 0.5 g |
| $MgSO_4.7H_2O$ | about 3 g |
| L-tyrosine | about 0.25 g |
| Chloline.Cl | about 0.1 g |
| Carbon source | between about 1 and about 100 g |
| Amino acid cocktail | between about 50 and about 150 mL |
| Vitamin solution | about 30 mL |
| Trace element solution | about 20 mL |
| UCON LB-625 antifoam | about 0.3 mL | wherein the amino acid cocktail contains (about g/L in the stock solution): L-arginine, 2.0; L-histidine, 1.0; L-isoleucine, 6.0; L-lysine, 4.0; methionine, 1.0; L-phenylalanine, 6.0; L-tryptophan, 4.0;

the vitamin solution contains (about mg/L in the stock solution): biotin, 10; Ca.pantothenate, 120; myo-inositol, 600; pyridoxine.HCl, 120; thiamine.HCl, 120;

the trace element solution contains (about mg/L in the stock solution): $FeSO_4.7H_2O$, 278; $ZnSO_4.7H_2O$, 288; $CuSO_4.5H_2O$, 80; $Na_2MoO_4.2H_2O$,242; $CoCl_2.6H_2O$, 238; $MnCl_2.2H_2O$, 198; and the carbon source is selected from the group consisting of glucose, sucrose, fucose, fructose, glycerol, ethanol, formic acid, lactic acid and combinations thereof.

2. The medium of claim 1 further comprising at least one additional component selected from the group consisting of succinic acid/NaOH about 10 g, adenine about 150 to about 400 mg, and uracil about 400 mg.

3. A method of culturing a strain of *Saccharomyces cerevisiae* in the medium of claim 1 comprising:

a) providing a portion of a medium of claim 1, b) inoculating said medium with a strain of *Saccharomyces cerevisiae*, and c) culturing said strain.

4. The method of claim 3 wherein the strain of *Saccharomyces cerevisiae* contains a recombinant DNA molecule.

5. The method of claim 4 which further comprises cultivating the strain of *Saccharomyces cerevisiae* under conditions that permit expression of the recombinant DNA molecule to product a recombinant protein.

6. The method of claim 5 which further comprises recovering the recombinant protein.

7. The method of claim 6 wherein the recombinant DNA molecule comprises a gene encoding hepatitis B surface antigen.

8. The method of claim 7 wherein the recombinant protein is hepatitis B surface antigen.

* * * * *